United States Patent [19]

Yoshizawa et al.

[11] Patent Number: 4,792,607
[45] Date of Patent: Dec. 20, 1988

[54] 5-FLUORO-3,4-DIHYDRO-2,4-DIOXO-N-(3-INDOLYL)-1(2H)-PYRIMIDINECARBOXAMIDES

[75] Inventors: Ryo Yoshizawa, Yokosuka; Masatoshi Kawashima, Yokohama; Hitoshi Yano, Kawasaki, all of Japan

[73] Assignee: Chisso Corporation, Osaka, Japan

[21] Appl. No.: 33,497

[22] Filed: Apr. 2, 1987

[30] Foreign Application Priority Data

Apr. 2, 1986 [JP] Japan .................................. 61-74297
Feb. 3, 1987 [JP] Japan .................................. 62-21727

[51] Int. Cl.$^4$ .......................................... C07D 403/02
[52] U.S. Cl. .................................... 544/310; 544/311
[58] Field of Search ................. 544/310, 311; 514/252

[56] References Cited

U.S. PATENT DOCUMENTS 4,349,552  9/1982  Takaya et al. .................... 544/311

FOREIGN PATENT DOCUMENTS 8072569  4/1983  Japan .................................. 544/311

OTHER PUBLICATIONS

Ozaki et al., CA 90-54966w.
Tokyo Metal Industries, CA 95-25106p.
Ozaki et al., CA 106-66979q.

Primary Examiner—Donald G. Daus
Assistant Examiner—Cecilia Shen
Attorney, Agent, or Firm—Wenderoth, Lind & Ponack

[57] ABSTRACT

5-Fluorouracil derivatives of this invention are represented by the general formula:

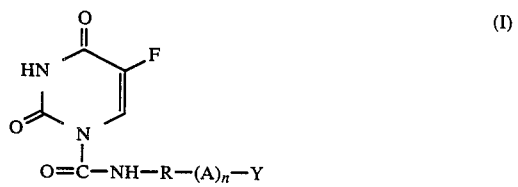

(I)

wherein R indicates an alkylene group having 1–8 carbon atoms, A indicates an atomic group of —NH— and —CO—, n is 0 or 1, and Y indicates an alkyl group having 1–10 carbon atoms, an aryl group, a heteroaryl group, a pyridinium ion having a halogen as a pair ion or an isocyanate group.

These derivatives are useful as anticancer medicines and intermediates therefor.

These derivatives are produced by six specified methods of this invention. A representative method is a process which comprises reacting 5-fluorouracil and an isocyanate represented by a general formula:

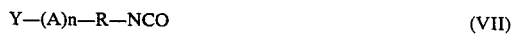

Y—(A)$_n$—R—NCO  (VII)

wherein R, A, n and Y are the same as those indicated in the formula (I).

5 Claims, No Drawings

5-FLUORO-3,4-DIHYDRO-2,4-DIOXO-N-(3-INDOLYL)-1(2H)-PYRIMIDINECARBOXAMIDES

BACKGROUND OF THE INVENTION

1. Fields of the Invention

This invention relates to new 5-fluorouracil derivatives useful for an anticancer medicine or intermediates thereof and processes for producing thereof.

2. Description of the Prior Art

Hitherto, 5-fluorouracil and its derivatives such as 1-(2-tetrahydrofuranyl)-5-fluorouracil, 1-hexylcarbamoyl-5-fluorouracil, etc. has been known an anticancer medicines.

However, as these compounds have toxicity, they exert a bad influence upon a living body. In case of doses for oral administration, there are disadvantages of digestive troubles. For this reason, when these compounds are dosed as an anticancer medicine, they need to have lower toxicity. In case of being lower in toxicity, the anticancer effect is lower, so that there is a problem that the anticancer medicine must be dosed in large quantities. Further, it is difficult to refine a desired product and to get a purified compound.

SUMMARY OF THE INVENTION

The purpose of this invention is to offer an anticancer medicine which has the anticancer effect and lower toxicity as a purified product.

Namely, this invention provides 5-fluorouracil derivatives represented by the general formula:

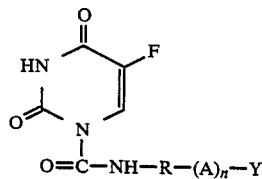

(I)

wherein R indicates a covalent bond, $-(CH_2)_m-$: m=1-8 or $-CH(CO_2C_2H_5)CH_2-$, A indicates an atomic group of $-NH-$ and $-CO-$, n is 0 or 1, and Y indicates an alkyl group having 1–10 carbon atoms, an aryl group, a heteroaryl group, a pyridinium ion having a halogen as a pair ion or an isocyanate group.

The compounds of this invention are new and useful for an anticancer medicine or an intermediate thereof which has the antitumor effect.

This invention also provides processes for producing 5-fluorouracil derivatives represented by the general formula (I).

The compounds of this invention are produced by the following processes.

The first method is a process of reacting 5-fluorouracil and an isocyanate represented by a general formula:

$$Y-(A)_n-R-NCO \quad \text{(VII)}$$

wherein R, A, n and Y are the same groups and numbers as those indicated in the formula (I). This reaction is illustrated in the following equation.

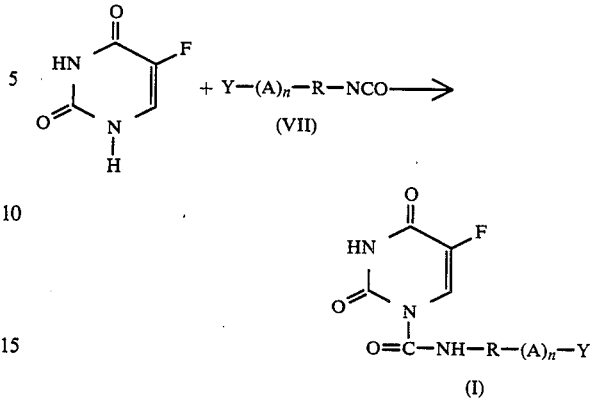

As the isocyanate (VII) which is used in this process, 2-thienyl isocyanate, 2-thiazolyl isocyanate, 2-chloroethyl isocyanate, 3-chloropropyl isocyanate, 5-bromopentyl isocyante, 1-oxopyridine-3-isocyanate, 3indolylmethyl isocyanate, benzamidomethyl isocyanate, nicotinamidomethyl isocyanate, ethylene diisocyanate, 1,3-trimethylene diisocyanate, 1,6-hexamethylene diisocyanate, 1,10-decamethylene diisocyanate, 2-isocyanatoethylpyridinium chloride, 5-isocyanatoheptyl pyridinium bromide, 7-isocyanatoheptylpyridinium iodide, 2-(3-phenylureido)ethyl isocyanate, 3-[3-(pyridine-3-yl)ureido]propyl isocyanate, 6-[3-(pyridine-3-yl)ureido]hexyl isocyanate, 6-[3-(4-sulfamoylphenyl)ureidio]hexyl isocyanate, 6-(3-nicotinamidoureido)-hexyl isocyanate, 6-(3-hexylureido)hexyl isocyanate, 6-[3-(3-dimethylaminopropyl)ureido]hexyl isocyanate, etc. can be exemplified.

These isocyanates can be commercially obtained or produced by suitable processes to be used appropriately.

As a suitable process, a process for producing from amine and dichlorocarbonyl, a process for producing from the corresponding carboxylic acid azide by the Curtius method, a process for producing from the corresponding amine and trichloromethylchloro formate, a process for producing from the corresponding olefin and isocyanic acid, etc. can be exemplified.

The ratio of 5-fluorouracil to the isocyanate preferably varies from 1.5:1 to 1:1.5 mole.

As reaction solvent, benzene, toluene, tetrahydrofuran, dioxane, acetonitrile, dimethyl formamide, dimethyl sulfoxide, ethyl acetate, chloroform, pyridine, triethylamine, etc. can be exemplifed.

The range of reaction temperature is 40°–100° C. To obtain the conclusion of the reaction, the final temperature is preferably above 80° C.

Reaction time varies depending on the reactivity of isocyanate. The range is suitably from 0.5 to 24 hours.

The second method is a process obtained by reacting 5-fluorouracil and a carboxylic acid azide represented by the corresponding formula:

$$Y-(A)_n-R-CON_3 \quad \text{(VIII)}$$

wherein R, A, n and Y are the same as those indicated in the formula (I). This reaction is illustrated in the following equation.

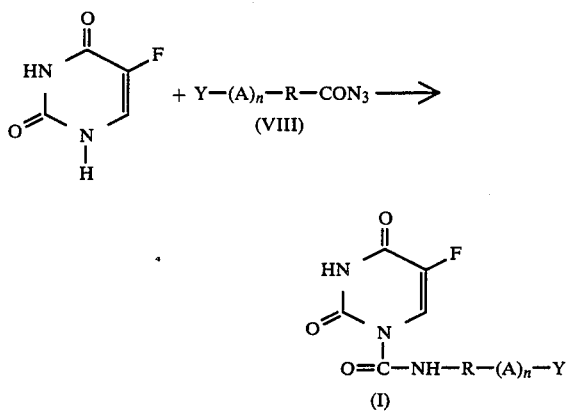

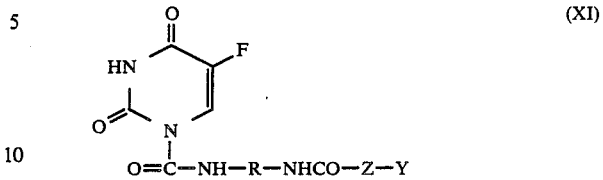

wherein R, Z and Y are the same as those indicated in the above formula.

This reaction is illustrated in the following equation.

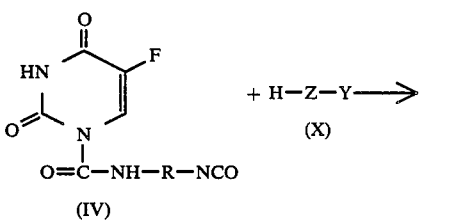

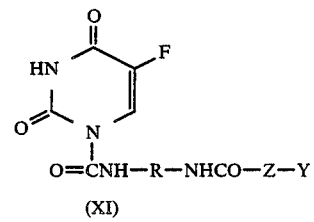

The 5-fluorouracil derivative (IV) having the isocyanate group, when Y of the isocyanate Y—(A)$_n$—R—NCO (VII) is isocyanate group (—NCO) and n=0, can be readily obtained. The compound (IV) is preferably used after isolation and purification of reaction mixture. However, it can be used as a crude compound or a reaction mixture.

The compound represented by the general formula (X) which is used in this reaction can be readily obtained. As the compound, hexylamine, N,N-dimethyl 1,3-propanediamine, phenethylamine, aniline, 2-aminopyridine, 3-aminopyridine, 2-aminothiazole, 2-aminodiazole, 4-aminobenzenesulfonamide, benzoylhydrazide, picolinoylhydrazide, nicotinoylhydrazide, etc. can be exemplified.

The ratio of the compound represented by the general formula (IV) to the compound represented by the general formula (X) is preferably 1.5:1 to 1:1.5 by mole. As reaction solvent, benzene, toluene, tetrahydrofuran, dioxane, acetonitrile, dimethyl formamdide, dimethyl sulfoxide, ethyl acetate, chloroform, pyridine, triethylamine, etc. can be exemplified.

The range of reaction temperature is 40°–100° C.

Reaction time varies depending on the reactivity of the compound (IV) and the compound (X). The range is suitably from 0.5 to 24 hours.

The fourth method is a process for reacting a 5-fluorouracil derivative represented by the general formula:

As the carboxylic acid azide (VIII) which is used in this process, 2-thenoyl azide, 2-thiazolylcarbonyl azide, 3-chloropropionyl azide, 6-bromohexanoyl azide, 4-chlorobutyryl azide, 1-oxopyridine-3-carbonyl azide, indol-3-carbonyl azide, indol-3-acetyl azide, benzamidoacetyl azide, succinyl diazide, glutaryl diazide, octanedioyl diazide, dodecandioyl diazide, pylidinium-1-propionyl azide chloride, pylidinium-1-hexanoyl azide bromide, pylidinium-1-octanoyl azide iodide, 3-(3-phenylureidopropionyl azide, 4-[3-(pyridine-3-yl)ureido]butyryl azide, 7-[3-(pyridine-2-yl)ureido]heptanoyl azide, 7-[3-(4-sulfamoylphenyl)ureido]heptanoyl azide, 7-(3-nicotinamidoureido]heptanoyl azide, 7-[3-(3-hexylureido]heptanoyl azide, 7-[3-(3-dimethylaminopropyl)ureido]heptanoyl azide, etc. can be exemplified.

These carboxylic acid azides generally can be produced by the usual technique from a corresponding carboxylic acid, acid hydrazide, etc.

The ratio of 5-fluorouracil to the carboxylic acid azide preferably varies from 1.5:1 to 1:1.5 by mole.

As reaction solvent, benzene, toluene, tetrahydrofuran, dioxane, acetonitrile, dimethyl formamide, dimethyl sulfoxide, ethyl acetate, chloroform, pyridine, triethylamine, etc. can be exemplified.

The range of reaction temperature is 40°–100° C. To obtain the conclusion of the reaction, the final temperature is preferably above 80° C.

Reaction time varies depending on the reactivity of carboxylic acid azide. The range is suitably from 0.5 to 24 hours.

The third method is a process for reacting a 5-fluorouracil derivative containing an isocyanate group represented by the general formula (IV):

wherein R indicates alkylene group having 1-8 carbon atoms, and a compound represented by the formula:

wherein Y has the same meaning as in the general formula (I), and Z indicates —NH— or —NHNH—CO—

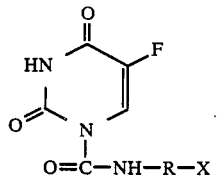

(XII)

wherein R indicates alkylene group having 1-8 carbon atoms and X indicates a halogen consisting of Cl, Br or I, and pyridine to obtain a 5-fluorouracil derivative represented by the general formula (III).

This reaction is illustrated in the following equation.

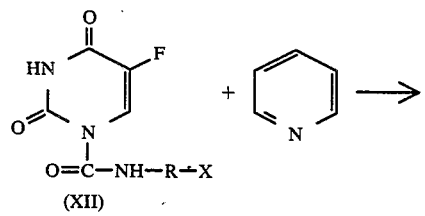

(XII)

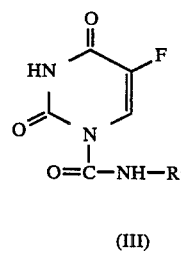

(III)

The 5-fluorouracil derivative (XII) used in this reaction, when Y of the isocyanate Y—(A)$_n$—R—NCO (VII) is a halogen (Cl, Br or I) and n=0, can be readily obtained by the reaction of the isocyanate (VII) with 5-fluorouracil.

The compound (XII) is preferably used after isolation and purification of the reaction product. However, it can be used as a crude compound or a reaction mixture.

The ratio of pyridine to the compound represented by the general formula (XII) is preferably above 1 by mole. Pyridine can be used as reaction solvent.

The range of reaction temperature is 30°-100° C.

Reaction time varies depending on the reactivity of the compound (XII). The range is suitably from 0.5 to 24 hours.

The fifth method for obtaining the compound of this invention is described.

In this method, the pyridinium compound (III) is produced by one step from three components of 5-fluorouracil, halogenoisocyanate: X—R—NCO (XIII) wherein R indicates alkylene group having 1-8 carbon atoms, and X is a halogen which is Cl, Br or I, and pyridine. This reaction is illustrated in the following equation.

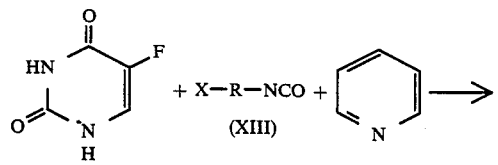

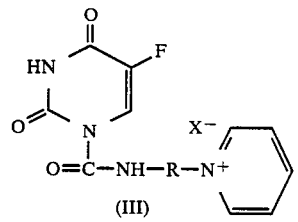

(III)

The ratio of 5-fluorouracil to the compound represented by the general formula (XIII) is preferably 1.5:1 to 1:1.5 by mole.

Above 1 by mole ratio of pyridine to the component having greater moles in said two components is preferable. As reaction solvent, pyridine is preferably used in excess.

The range of reaction temperature is 40°-100° C.

Reaction time is suitably from 0.5 to 24 hours. In case of less than 0.5 hours, the reaction to obtain the pyridinium is imcomplete because the reaction rate is small, and it is difficult to obtain the pure objective compound.

The sixth method is a process for reacting 1-chlorocarbonyl-5-fluorouracil (XIV) and a corresponding amine (XV) in a solvent as illustrated in the following equation,

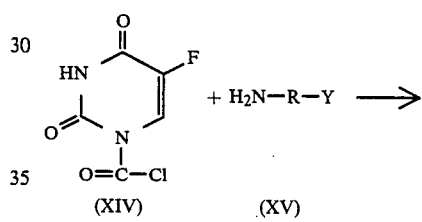

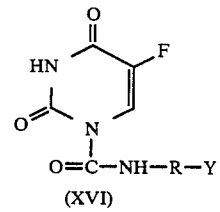

(XVI)

wherein R and Y indicate the same groups as those indicated in the general formula (I).

The 1-chlorocarbonyl-5-fluorouracil used in this reaction can be obtained by introducing e.g. dichlorocarbonyl into 5-fluorouracil in a basic solvent. This solution can be used as it is in the next reaction with the amine (XV).

As the amine which is used in this process, 3-(3-aminopropyl)indole, 3-(6-aminohexyl)indole, 1-methyl-3-aminomethyl indole, 1-methyl-3-(2-aminoethyl)indole, 2-methyl-3-aminomethyl indole, 2-methyl-3-(2-aminoethyl)indole, 4-methoxy-3-aminomethyl indole, 4-methoxy-3-(2-aminoethyl)indole, 5-methoxy-3-aminomethyl indole, 5-methoxy-3-(2-aminoethyl)indole, 4,5-dimethoxy-3-aminomethyl indole, 4,5-dimethoxy-3-(2-aminoethyl)indole, 5,6-dimethoxy-3-aminomethyl indole, 5,6-dimethoxy-3-(2-aminoethyl)indole, 4,6-dimethoxy-3-aminomethyl indole, 4,6-dimethoxy-3-(2-aminoethyl)indole, 4,5,6-trimethoxy-3-aminomethyl indole, 4,5,6-trimethoxy-3-(2-aminoethyl)indole, 4-hydroxy-3-aminomethyl indole, 4-hydroxy-3-(2-aminoethyl)indole, 5-hydroxy-3-aminomethyl indole, 5-hydroxy-3-(2-aminoethyl)indole, 5,6-dihydroxy-3-aminomethyl indole, 5,6-dihydroxy-3-(2-aminoethyl)indole, 5-amino-3-aminomethyl indole, 5-amino-3-(2-aminoethyl)indole, 5-nitro-3-aminomethyl indole, 5-nitro-3-(2-aminoethyl)indole, 5-chloro-3-aminomethyl indole, 5-chloro-3-(2-aminoethyl)indole, etc. can be exemplified.

The ratio of 1-chlorocarbonyl-5-fluorouracil to the amine is preferably 1.5:1 to 1:1.5 by mole.

As the reaction solvent, benzene, toluene, tetrahydrofuran, dioxane, acetonitrile, dimethyl formamide, dimethyl sulfoxide, ethyl acetate, chloroform etc. with basic solvent such as pyridine, triethylamine, etc. or the basic solvent alone can be used.

The reaction temperature range is 0°-30° C., preferably, 5°-15° C.

The reaction time is different by the reactivity of used amine, suitably from 0.5 to 5 hours.

As mentioned above, in these six processes, the residue obtained after distillation of a solvent under reduced pressure from the final result reactant, or the residue obtained by adding a suitable poor solvent is refined by extraction, recrystallization, chromatography, etc. to obtain the objective compound of this invention.

The compounds which can be the objective of this invention are exemplified:

5-fluoro-3,4-dihydro-2,4-dioxo-N-(2-thienyl)-1(2H)-pyrimidinecarboxamide,
5-fluoro-3,4-dihydro-2,4-dioxo-N-(2-thiazolyl)-1(2H)-pyrimidinecarboxamide,
5-fluoro-3,4-dihydro-2,4-dioxo-N-(2-oxopyridine-3-yl)-1(2H)-pyrimidinecarboxamide,
5-fluoro-3,4-dihydro-2,4-dioxo-N-(3-indolyl)-1(2H)-pyrimidinecarboxamide,
5-fluoro-3,4-dihydro-2,4-dioxo-N-(3-indolylmethyl)-1(2H)-pyrimidinecarboxamide,
N-benzamidomethyl-5-fluoro-3,4-dihydro-2,4-dioxo-1(2H)-pyrimidinecarboxamide,
5-fluoro-3,4-dihydro-2,4-dioxo-N-nicotinamidomethyl-1(2H)-pyrimidinecarboxamide,
5-fluoro-3,4-dihydro-2,4-dioxo-N-[2-(1-pyridinio)ethyl]-1(2H)-pyrimidinecarboxamide chloride,
5-fluoro-3,4-dihydro-2,4-dioxo-N-[3(1-pyridinio)propyl]-1(2H)-pyrimidinecarboxamide chloride,
5-fluoro-3,4-dihydro-2,4-dioxo-N-[7-(1-pyridinio)heptyl]-1(2H)-pyrimidinecarboxamide iodide,
5-fluoro-3,4-dihydro-2,4-dioxo-N-(2-isocyanatoethyl)-1(2H)-pyrimidinecarboxamide,
5-fluoro-3,4-dihydro-2,4-dioxo-N-(3-isocyanatopropyl)-1(2H)-pyrimidinecarboxamide,
5-fluoro-3,4-dihydro-2,4-dioxo-N-(6-isocyanatohexyl)-1(2H)-pyrimidinecarboxamide,
5-fluoro-3,4-dihydro-2,4-dioxo-N-(3-phenylureido)-1(2H)-pyrimidinecarboxamide,
5-fluoro-3,4-dihydro-2,4-dioxo-N-{6-[3(3-pyridinyl)ureido]hexyl}-1(2H)-pyrimidinecarboxamide,
5-fluoro-3,4-dihydro-2,4-dioxo-N-{6-[3-(3-pyridyl)ureido]hexyl}-1(2H)-pyrimidinecarboxamide,
5-fluoro-3,4-dihydro-2,4-dioxo-N-{6-[3-(4-sulfamoylphenyl)ureido]hexyl}-1(2H)-pyrimidinecarboxamide,
5-fluoro-3,4-dihydro-2,4-dioxo-N-[6-(3-hexylureido)hexyl]-1(2H)-pyrimidinecarboxamide,
5-fluoro-3,4-dihydro-2,4-dioxo-N-{6-[3-(3-dimethylaminopropyl)ureido[hexyl}-1(2H)-pyrimidinecarboxamide,
5-fluoro-3,4-dihydro-2,4-dioxo-N-[3-(2-thiazolyl)ureido]hexyl-1(2H)-pyrimidinecarboxamide,
N-[3-(2-diazolyl)ureido]hexyl-5-fluoro-3,4-dihydro-2,4-dioxo-N-1(2H)-pyrimidinecarboxamide,
5-fluoro-3,4-dihydro-2,4-dioxo-N-{6-[3-nicotinamidoureido]hexyl}-1(2H)-pyrimidinecarboxamide, and
5-fluoro-3,4-dihydro-2,4-dioxo-N-{6-[3-isonicotinamidoureido]hexyl}-1(2H)-pyrimidinecarboxamide.

It is found that the 5-fluorouracil derivatives of this invention are materials which have antitumor properties or are important intermediates from which can be obtained the antitumor materials. The antitumor effect of these 5-fluorouracil derivatives is shown in Table 1. It is clear from the Table that P-388 Leukemia of a laboratory mouse having a tumor is predominantly controlled.

The effects of this invention are as follows.

According to this invention, it is able to offer an anticancer medicine which has the anticancer effect and lower toxicity. Therefore, the medicine does not have a bad influence upon a living body. Furthermore, it does not have a problem that the medicine is hard on the stomach in case of oral administration. Then, when the medicine is produced by this invention method, purer object is obtained than that obtained by the conventional method.

DESCRIPTION OF THE PREFERRED EMBODIMENTS

The following examples illustrate this invention more specifically.

EXAMPLE 1

5-Fluoro-3,4-dihydro-2,4-dioxo-N-(2-thienyl)-1(2H)-pyrimidinecarboxamide:

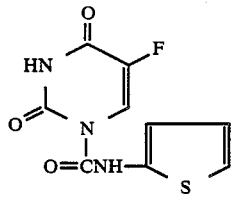

2-Thienyl isocyanate (3.09 g, 24.7 mmol) and 5-fluorouracil (3.21 g, 24.7 mmol) were added into a solvent of benzene (50 ml) and pyridine (20 ml), and stirred and refluxed at 80° C. for 16 hours.

After cooling the reactant, obtained crystals were filtered, and washed with a mixed solvent of benzene:pyridine (3:2), subsequently washed with a mixed solvent of benzene:ethanol (3:2), and vacuum-dried. 5-Fluoro-3,4-dihydro-2,4-dioxo-N-(2-thienyl)-1(2H)-pyrimidinecarboxamide (5.00 g, 19.6 mmol) is obtained.

Yield: 79.3%, Melting point: 166°~175° C.

$IR_{max}$ (KBr disk): 3430(N—H), 3090, 3050(=CH—), 1735, 1712(> =0), 1260(=CF—), 702(=C—S) [cm$^{-1}$].

Element analysis: Found C 42.39, H 2.42, N 16.50 [%]; Calculated [for $C_9H_6FN_3O_3S$]: C42.35, H 2.37, N 16.46 [%].

EXAMPLE 2

5-Fluoro-3,4-dihydro-2,4-dioxo-N-(1-oxopyridine-3-yl)-1(2H)-pyrimidinecarboxamide:

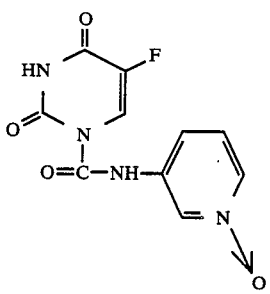

3-(1-Oxopyridyl)carbonyl azide (3.72 g, 22.7 mmol) and 5-fluorouracil (3.00 g, 23.1 mmol) were added into pyridine (45 ml), and stirred and reacted at 90° C. for one hour. After cooling the reactant, obtained crystals were filtered, washed with hot methanol, and vacuum-dried. 5-Fluoro-3,4-dihydro-2,4-dioxo-N-(1-oxopyridine-3-yl)-1(2H̲)-pyrimidinecarboxamide (5.48 g, 20.7 mmol) was obtained.

Yield: 91%, Melting point: 243°~246° C.

$IR_{max}$ (KBr disk): 3460(NH), 3120, 3080 (=CH—), 1700~1760(>=O), 1280(N—O), 1250(=CF—) [$cm^{-1}$].

Element analysis: Found C 45.17, H 2.33, N 21.23 [%]; Calculated [for $C_{10}H_6N_4O_4F$]: C 45.29, H 2.28, N 21.13 [%].

EXAMPLE 3

5-Fluoro-3,4-dihydro-2,4-dioxo-N-(3-indolyl)-1(2H̲)-pyrimidinecarboxamide:

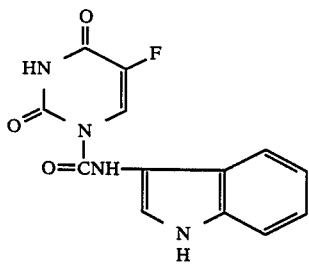

3-Indolylcarbonyl azide (1.73 g, 9.29 mmol) and 5-fluorouracil (1.20 g, 9.23 mmol) were added into a mixed solvent of benzene (15 ml) and pyridine (3 ml), and stirred and refluxed at 80° C. for 24 hours.

After cooling the reactant, obtained crystals were filtered, washed with benzene, subsequently washed with hot methanol, and vacuum-dried. 5-Fluoro-3,4-dihydro-2,4-dioxo-N-(3-indolyl)-1(2H̲)-pyrimidinecarboxamide (2.06 g, 7.15 mmol) was obtained.

Yield: 77%, Melting point: 246°~250° C.

$IR_{max}$ (KBr disk): 3430, 3370, 3340, 3200(NH), 3100(=CH—), 1760, 1730, 1695(>=O), 1235(=CF—) [$cm^{-1}$].

Element analysis: Found C 53.99 H 2.96, N 19.39 [%]; Calculated [for $C_{13}H_9N_4O_3F$]: C 54.17, H 3.15, N 19.44 [%].

EXAMPLE 4

5-Fluoro-3,4-dihydro-2,4-dioxo-N-(3-indolylmethyl)-1(2H̲)-pyrimidinecarboxamide:

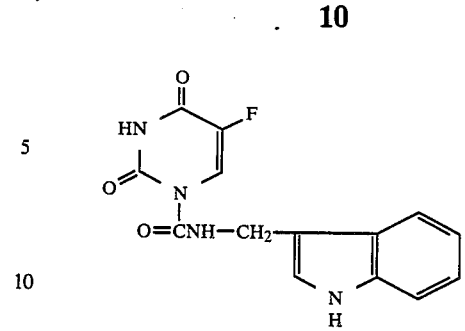

3-Indolylacetohydrazide (6.90 g, 36.5 mmol) and concentrated hydrochloric acid (4.4 ml) were added into water (800 ml), and added sodium nitrite at 5°~10° C. The obtained acid azide was extracted in benzene, washed with water, and dried with anhydrous sodium sulfate. The obtained solution was concentrated into about 100 ml. 5-Fluorouracil (4.70 g, 36.1 mmol) and pyridine (50 ml) were added into benzene solution of this acid azide, and stirred and refluxed at 80° C. for one hour.

After cooling the reactant, obtained crystals were filtered and washed with methanol. Subsequently, the crystals were dissolved into tetrahydrofuran, insoluble parts were removed, and then the obtained solution was concentrated under reduced pressure. The obtained crystals were washed with methanol, and vacuum-dried. 5-Fluoro-3,4-dihydro-2,4-dioxo-N-(3-indolylmethyl)-1(2H̲)-pyrimidinecarboxamide (2.11 g, 6.98 mmol) was obtained.

Yield: 19%, Melting point: 176°~177° C.

$IR_{max}$ (KBr disk): 3440, 3300, 3200(NH), 3120 (=CH—), 1740, 1690~1720(>=O), 1235(=CF—) [$cm^{-1}$].

Element analysis: Found C 55.29 H 3.65, N 18.09 [%]; Calculated [for $C_{14}H_{11}FN_4O_3$]: C 55.59, H 3.67, N 18.60 [%].

EXAMPLE 5

5-Fluoro-3,4-dihydro-2,4-dioxo-N-(3-indolylmethyl)-1(2H̲)-pyrimidinecarboxamide:

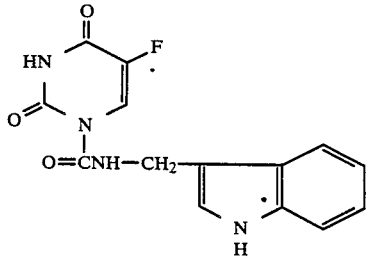

5-Fluorouracil (2.00 g, 15.4 mmol) was suspended into pyridine (60 ml). A little excess dichlorocarbonyl was blown into the suspension and stirred well at 0°~5° C. After raising to 10° C., $N_2$ was blown into the reaction mixture, and nonreacted excess dichlorocarbonyl was removed. After recooling to 0° C., 3-aminomethylindole (2.30 g, 15.7 mmol) in pyridine (20 ml) was dropped into the reactant.

After stirring the reactant and raising the temperature for one hour to room temperature, the solvent was distilled under reduced pressure.

Chloroform (20 ml) and 1N hydrochloric acid (50 ml) were added into the residue. The obtained solids were washed with water and then methanol, and vacuum-dried. 5-Fluoro-3,4-dihydro-2,4-dioxo-N-(3-indolylmethyl)-1(2H)-pyrimidinecarboxamide (1.63 g, 5.39 mmol) was obtained.

Yield: 35%, Melting point: 176°~178° C.

IR$_{max}$ (KBr disk): 3440, 3300, 3200(NH), 3120 (=CH—), 1740, 1690~1720(>=0), 1235(=CF—) [cm$^{-1}$].

Element analysis: Found C 55.68 H 3.50, N 18.25 [%]; Calculated [for C$_{14}$H$_{11}$FN$_4$O$_3$]: C 55.59, H 3.67, N 18.60 [%].

EXAMPLE 6

5-Fluoro-3,4-dihydro-2,4-dioxo-N-(5-fluoroindole-3-yl)methyl-1(2H)-pyrimidinecarboxamide:

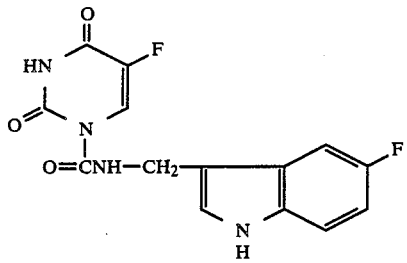

5-Fluorouracil (6.10 g, 46.9 mmol) was suspended into pyridine (180 ml). A little excess dichlorocarbonyl was blown into the suspension stirring will at 0°~5° C. After raising the temperature to 10° C., N$_2$ was blown into the reaction mixture, and nonreacted excess dichlorocarbonyl was removed. After recooling to 0° C., 5-fluoro-3-aminomethylindole (7.7 g, 46.9 mmol) in pyridine (50 ml) was dropped into the reactant.

After stirring the reactant and raising the temperature for one hour to room temperature, the solvent was distilled under reduced pressure.

Water (100 ml) was added into the residue and stirred to obtain solids. The solids were washed with water and then chloroform, and dissolved in tetrahydrofuran. The solution was decolored with active carbon, dried with anhydrous magnesium sulfate, and filtered. The filtrate was concentrated. 5-Fluoro-3,4-dihydro-2,4-dioxo-N-(5-fluoroindole-3-yl)methyl-1(2H)-pyrimidinecarboxamide (2.25 g, 7.03 mmol) was obtained.

Yield: 15%, Melting point: 162°~166° C.

$^1$H—NMR (CD$_3$SOCD$_3$—CD$_3$COCD$_3$—TMS): δ [ppm]; 4.67(d; J=5.5 Hz, —CH$_2$—, 2H), 6.7~7.8(m; Ar—H, 4H), 8.3(brs; —NH—, 1H), 8.40(d; J=7.5 Hz, —CF=CH—, 1H), 9.4(brs; —NH—, 1H), 11.0(brs; —NH—, 1H).

IR$_{max}$ (KBr disk) [cm$^{-1}$]; 3420, 3310(NH), 3100(=CH—), 1740, 1700, 1670 (>=0).

Element analysis: Found C 52.01, H 3.13, N 17.09 [%] Calculated [for C$_{14}$H$_{10}$F$_2$N$_4$O$_3$]: C 52.51, H 3.15, N 17.49 [%].

EXAMPLE 7

5-Fluoro-3,4-dihydro-2,4-dioxo-N-[2-(4,5,6-trimethoxyindole-3-yl)ethyl]-1(2H)-pyrimidinecarboxamide:

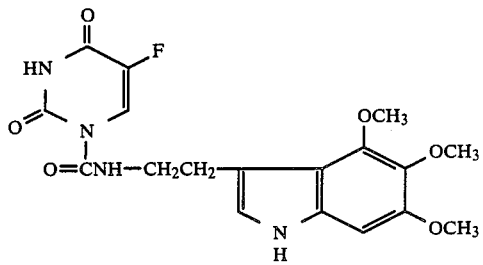

5-Fluorouracil (1.91 g, 14.7 mmol) was suspended into pyridine (80 ml). A little excess dichlorocarbonyl was blown into the suspension stirring well at 0°~5° C. After raising the temperature to 10° C., N$_2$ was blown into the reaction mixture, and nonreacted excess dichlorocarbonyl was removed. After recooling to 0° C., 4,5,6-trimethoxy-3-(2-aminoethyl)indole (3.67 g, 14.7 mmol) in pyridine (20 ml) was dropped into the reactant.

After stirring the reactant and raising the temperature for one hour to room temperature, the solvent was distilled under reduced pressure. The residue was washed with water, chloroform, and then methanol. 5-Fluoro-3,4-dihydro-2,4-dioxo-N-[2-(4,5,6-trimethoxyindole-3-yl)ethyl-1(2H)-pyrimidinecarboxamide (1.29 g, 3.17 mmol) was obtained.

Yield: 22%, Melting point: 172°~174° C.

$^1$H—NMR (CD$_3$SOCD$_3$—TMS): δ [ppm]; 3.00(t; J=6 Hz, —CH$_2$—, 2H), 3.60(t; J=6 Hz, —CH$_2$—, 2H), 3.70(S; —CH$_3$, 3H), 3.78(S; —CH$_3$, 3H), 3.90(S; —CH$_3$, 3H), 6.6~7.0(m; Ar—H, 2H), 8.35(d; J=7 Hz, —CF=CH—, 1H), 9.25(brs; —NH—, 1H), 10.53(brs; —NH—, 1H), 12.30(brs; —NH—, 1H).

IR$_{max}$ (KBr disk) [cm$^{-1}$]; 3420(NH), 3100(=CH—), 1740, 1700, 1675 (>=0), 1100(C—O—C).

EXAMPLE 8

5-Fluoro-3,4-dihydro-2,4-dioxo-N-[1-ethoxycarbonyl-2-(3-indolyl)ethyl]-1(2H)-pyrimidinecarboxamide:

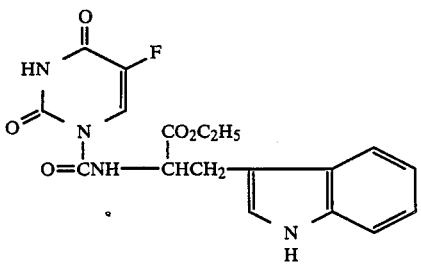

. 5-Fluorouracil (5.93 g, 45.6 mmol) was suspended into pyridine (100 ml). A little excess dichlorocarbonyl was blown into the suspension and stirred well at 0°~5° C. After raising the temperature to 10° C., N$_2$ was blown into the reaction mixture, and nonreacted excess dichlorocarbonyl was removed. After recooling to 0° C., tryptophane ethyl ester (10.5 g, 45.2 mmol) in pyridine (50 ml) was dropped into the reactant.

After stirring the reactant and raising the temperature for 30 minutes to room temperature, the solvent was distilled under reduced pressure. The obtained crystals were washed with methanol, and vacuum-dried. 5-Fluoro-3,4-dihydro-2,4-dioxo-N-[1-ethoxycarbonyl-2-

(3-indolyl)ethyl]-1(2H)-pyrimidinecarboxamide (8.34 g, 21.5 mmol) was obtained.

Yield: 48%, Melting point: 250°~258° C.

$^1$H—NMR (CD$_3$SOCD$_3$—TMS): δ [ppm]; 1.16 (t; J=7 Hz, —CH$_3$, 3H), 3.15~3.5 (m; —CH$_2$—, 2H), 4.10(q; J=7 Hz, —CH$_2$—, 2H), 4.5~5.0(m; —CH—, 1H), 6.8~7.65(m; Ar—H, —NH—, 6H), 8.37 (d; J=7 Hz, —CF=CH—, 1H), 9.65(d; J=6 Hz, —NH—, 1H), 10.92(brs; —NH—, 1H), IR$_{max}$ (KBr disk) [cm$^{-1}$]; 3430, 3280 (NH), 1750, 1725, 1695 (>=0).

Element analysis: Found C 55.65, H 4.44, N 14.59 [%]; Calculated [for C$_{18}$H$_{17}$FN$_4$O$_5$]: C 55.67, H 4.41, N 14.43 [%].

EXAMPLE 9

5-Fluoro-3,4-dihydro-2,4-dioxo-N-([2-(2-methylindole-3-yl)ethyl]-1(2H)-pyrimidinecarboxamide:

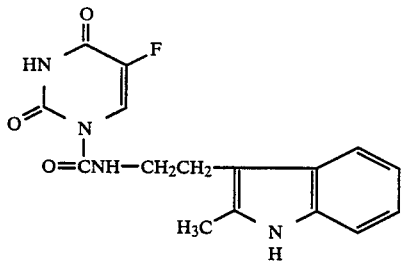

5-Fluorouracil (4.44 g, 34.1 mmol) was suspended into pyridine (150 ml). A little excess dichlorocarbonyl was blown into the suspension and stirred well at 0°~5° C. After raising the temperature to 10° C., N$_2$ was blown into the reaction mixute, and nonreacted excess dichlorocarbonyl was removed. After recooling to 0° C., 2-methyl-3-(2-aminoethyl)indole (5.94 g, 34.1 mmol) in pyridine (150 ml) was dropped into the reactant.

After stirring the reactant and raising the temperature for one hour to room temperature, the solvent was distilled under reduced pressure. The residue was dissolved into methanol (30 ml) and 1N HCl (100 ml) was added to the solution. After stirring the solution, viscous oil was obtained. After removing the supernatant liquid, chloroform (50 ml) was added into the oil to obtain crystals. The crystals were washed with water, methanol, and then chloroform, and dried under reduced pressure. 5-Fluoro-3,4-dihydro-2,4-dioxo-N-[2-(2-methylindole-3-yl)ethyl]-1(2H)-pyrimidinecarboxamide (2.94 g, 8.90 mmol) was obtained.

Yield: 26%, Melting point: 163°~166° C.

$^1$H—NMR (CD$_3$SOCD$_3$—TMS): δ [ppm]; 2.37 (s; —CH$_3$, 3H), 2.94(t; J=6 Hz, —CH$_2$—, 2H), 3.2~3.8 (m; —CH$_2$—, 2H), 6.83~7.70(m; Ar—H, —NH—, 5H), 8.34(d; J=7 Hz, —CF=CH—, 1H), 9.32 (t; J=5 Hz, —NH—, 1H), 10.65(brs; —NH—, 1H), IR$_{max}$ (KBr disk) [cm$^{-1}$]; 3440, 3370, 3310, 3220(NH), 3120(=CH—), 1730, 1710 (>=0)

Element analysis: Found C 57.90, H 4.70, N 16.71 [%]; Calculated [for C$_{16}$H$_{15}$FN$_4$O$_3$]: C 58.18, H 4.58, N 16.96 [%].

EXAMPLE 10

5-Fluoro-3,4-dihydro-2,4-dioxo-N-(5-methoxyindole-3-yl)methyl-1(2H)-pyrimidinecarboxamide:

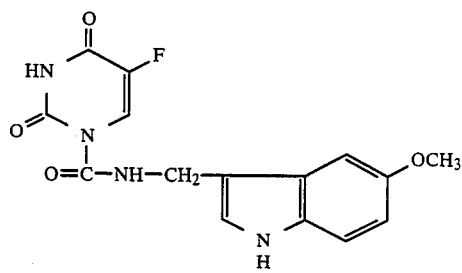

5-Fluorouracil (2.93 g, 22.5 mmol) was suspended into pyridine (90 ml). A little excess dichlorocarbonyl was blown into the suspension and stirred well at 0°~5° C. After raising the temperature to 10° C., N$_2$ was blown into the reaction mixture, and nonreacted excess dichlorocarbonyl was removed. After recooling to 0° C., 5-methoxy-3-aminomethylindole (3.97 g, 22.5 mmol) in pyridine (30 ml) was dropped into the reactant.

After stirring the reactant and raising the temperature for one hour to room temperature, the solvent was distilled under reduced pressure. To the residue 20 ml of chloroform and 70 ml of 1N HCl were added. After stirring the solution, crystals were obtained. The crystals were washed with water and then methanol. 5-Fluoro-3,4-dihydro-2,4-dioxo-N-(5-methoxyindole-3-yl)methyl-1(2H)-pyrimidinecarboxamide (3.33 g, 10.0 mmol) was obtained.

Yield: 44%, Melting point: 145°~151° C.

$^1$H—NMR (C$_5$D$_5$N—TMS): δ [ppm]; 3.83 (s; —OCH$_3$—, 3H), 4.95(d; J=5 Hz, —CH$_2$—, 2H), 6.86~7.60(m; Ar—H, 4H), 8.62(d; J=7 Hz, —CF=CH—, 1H), 8.93(brs; —NH—, 1H), 8.87(t; J=5 Hz, —NH—, 1H), 11.73(brs; —NH—, 1H), IR$_{max}$ (KBr disk) [cm$^{-1}$]; 3440, 3320, 3210(=CH—), 1740, 1720~1670 (>=0).

Element analysis: Found C 54.29, H 3.93, N 16.57 [%]; Calculated [for C$_{15}$H$_{13}$FN$_4$O$_4$]: C 54.22, H 3.94, N 16.86 [%]

EXAMPLE 11

5-Fluoro-3,4-dihydro-2,4-dioxo-N-(5-chloroindole-3-yl)methyl-1(2H)-pyrimidinecarboxamide:

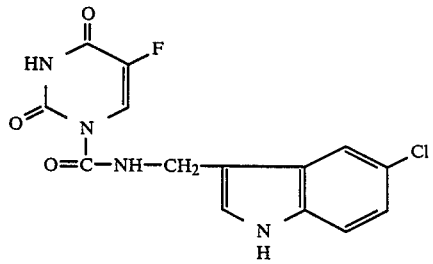

5-Fluorouracil (5.53 g, 42.5 mmol) was suspended into pyridine (160 ml). A little excess dichlorocarbonyl was blown into the suspension and stirred well at 0°~5° C. After raising the temperature to 10° C., N$_2$ was blown into the reaction mixture, and nonreacted excess dichlorocarbonyl was removed. After recooling to 0° C., 5-chloro-3-aminomethylindole (7.67 g, 42.5 mmol) in pyridine (30 ml) was dropped into the reactant.

After stirring the reactant and raising the temperature for one hour to room temperature, the solvent was distilled under reduced pressure. The residue was dissolved into methanol (50 ml), and then 1N HCl (50 ml) was added. After stirring the solution, solids were obtained. The solids were washed with water and dissolved in ethyl ether. The solution was decolored with active carbon, dried with anhydrous sodium sulfate, and filtered. The filtrate was concentrated. The obtained crystals was dissolved in ethyl ether. Insoluble parts were filtered. Hexane was added into the filtrate, and crystals were obtained. 5-Fluoro-3,4-dihydro-2,4-dioxo-N-(5-chloroindole-3-yl)methyl-1(2H)-pyrimidinecarboxamide (1.10 g, 3.27 mmol) was obtained.

Yield: 8%, Melting point: 101°~105° C.

$^1$H—NMR (CD$_3$COCD$_3$—TMS): δ [ppm]; 4.70(d; J=5.5 Hz, —CH$_2$—, 2H), 6.8~7.8(m; Ar—H, 4H), 8.42 (d; J=7 Hz, —CF=CH—, 1H), 8.5(brs; —NH—, 1H), 10.05(brs; —NH—, 1H).

IR$_{max}$ (KBr disk) [cm$^{-1}$]; 3440, 3350(NH), 3100(=CH—), 1745, 1700, 1680 (>=0).

Element analysis: Found C 50.34, H 3.32, N 16.35 [%]; Calculated [for C$_{14}$H$_{10}$ClFN$_4$O$_3$]: C 49.94, H 2.99, N 16.64 [%].

EXAMPLE 12

5-Fluoro-3,4-dihydro-2,4-dioxo-N-[2-(5-chloroindole-3-yl)ethyl]-1(2H)-pyrimidinecarboxamide:

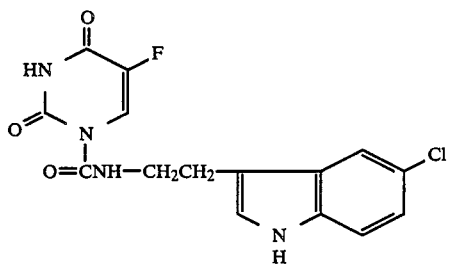

5-Fluorouracil (4.08 g, 31.4 mmol) was suspended into pyridine (120 ml). A little excess dichlorocarbonyl was blown into the suspension and stirred well at 0°~5° C. After raising the temperature to 10° C., N$_2$ was blown into the reaction mixture, and nonreacted excess dichlorocarbonyl was removed. After recooling to 0° C., 5-chloro-3-(2-aminoethyl)indole (6.11 g, 31.4 mmol) in pyridine (30 ml) was dropped into the reactant.

After stirring the reactant and raising the temperatures for one hour to room temperature, the solvent was distilled under reduced pressure. The residue was dissolved into chloroform, and then 0.5N HCl (50 ml) was added. After stirring the solution, insoluble matter was separated. This insoluble matter was washed with water and then chloroform, and dissolved in tetrahydrofuran. The solution was decolored with active carbon, dried with anhydrous magnesium sulfate, and filtered. The filtrate was passed through a short column of silica gel. Then, the obtained solution was concentrated to about 50 ml and added hexane (20 ml). The obtained crystals were washed with methanol. 5-Fluoro-3,4-dihydro-2,4-dioxo-N-[2(5-chloroindole-3-yl)ethyl]-1(2H)-pyrimidinecarboxamide (2.79 g, 7.95 mmol) was obtained.

Yield: 25%, Melting point: 204°~206° C.

$^1$H—NMR (CD$_3$SOCD$_3$—CD$_3$COCD$_3$—TMS): δ [ppm]; 3.00(t; J=6 Hz, —CH$_2$—, 2H), 3.60(t; J=6 Hz, —CH$_2$—, 2H), 6.9~7.8(m; Ar—H, —NH—, 5H), 8.38(d; J=7 Hz, —CF=CH—, 1H), 9.25(brs; —NH—, 1H), 11.0(brs; —NH—, 1H).

IR$_{max}$ (KBr disk) [cm$^{-1}$]; 3450, 3320(NH), 3100(=CH—), 1750, 1700, 1670 (>=0).

Element analysis: Found C 51.56, H 3.50, N 15.47 [%]. Calculated [for C$_{15}$H$_{12}$ClFN$_4$O$_3$]: C 51.37, H 3.45, N 15.97 [%].

EXAMPLE 13

N-Benzamidomethyl-5-fluoro-3,4-dihydro-2,4-dioxo-1(2H)-pyrimidinecarboxamide:

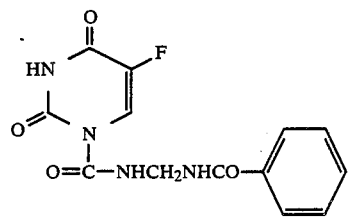

Benzamidoacetyl azide (7.30 g, 35.8 mmol) and 5-fluorouracil (3.90 g, 30.0 mmol) were added into benzene (20 ml) and pyridine (5 ml), and stirred and refluxed at 80° C. for 6 hours.

After cooling the reactant, obtained crystals were filtered, washed with chloroform, subsequently washed with methanol, and vacuum-dried. N-Benzamidomethyl-5-fluoro-3,4-dihydro-2,4-dioxo-1(2H)-pyrimidinecarboxamide (6.77 g, 22.1 mmol) was obtained.

Yield: 74%, Melting point: 196°~199° C.

IR$_{max}$ (KBr disk): 3425, 3330, 3230(NH), 3125 (=CH—), 1750, 1735(>=0), 1240(=CF—) [cm$^{-1}$].

Element analysis: Found C 50.98 H 3.44, N 18.25 [%]; Calculated [for C$_{13}$H$_{11}$N$_4$O$_4$F]: C 50.98, H 3.62, N 18.29 [%].

EXAMPLE 14

5-Fluoro-3,4-dihydro-2,4-dioxo-N-[2-(1-pyridino)ethyl]-1(2H)-pyrimidinecarboxamide chloride:

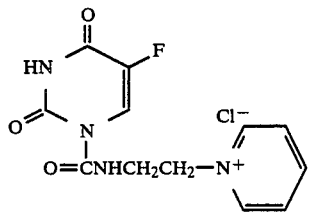

2-Chloroethyl isocyanate (4.71 g, 44.6 mmol) and 5-fluorouracil (5.80 g, 44.6 mmol) were added into pyridine (50 ml), and stirred and refluxed at 90° C. for 3.5 hours.

After cooling the reactant, obtained crystals were filtered, washed with chloroform, subsequently washed with methanol, and vacuum-dried. 5-Fluoro-3,4-dihydro-2,4-dioxo-N-[2-(1-pyridino)ethyl]-1(2H)-pyrimidinecarboxamide chloride (2.38 g, 7.56 mmol) was obtained.

Yield: 17%, Melting point: 212°~216° C.

IR$_{max}$ (KBr disk): 3430, 3350, 3270(NH), 3100, 3045 (=CH—), 1700~1740, 1690(>=0), 1260(=CF—) [cm$^{-1}$].

Element analysis: Found C 45.33, H 3.98, N 17.56 [%]; Calculated [for C$_{12}$H$_{12}$ClFN$_4$O$_3$]: C 45.80, H 3.84, N 17.80 [%].

EXAMPLE 15

5-Fluoro-3,4-dihydro-2,4-dioxo-N-[2-(1-pyridinio)ethyl]-1(2H)-pyrimidinecarboxamide chloride:

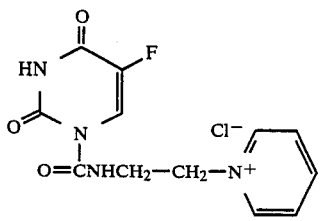

N-(2-Chloroethyl)-5-fluoro-3,4-dihydro-2,4-dioxo-1(2H)-pyrimidinecarboxamide (2.00 g, 8.49 mmol) were added into pyridine (10 ml), and stirred and refluxed at 90° C. for 6 hours.

After cooling the reactant, obtained crystals were filtered, washed with chloroform, subsequently washed with methanol, and vacuum-dried. 5-Fluoro-3,4-dihydro-2,4-dioxo-N-[2-(1-pyridinio)ethyl]-1(2H)-pyrimidinecarboxamide chloride (1.36 g, 4.32 mmol) was obtained.

Yield: 51%, Melting point: 213°~216° C.

IR$_{max}$ (KBr disk): 3430, 3350, 3270(NH), 3100, 3045(=CH—), 1700~1740, 1690(>=O), 1260(=CF—) [cm$^{-1}$].

Element analysis: Found C 45.53 H 4.07, N 17.68 [%]; Calculated [for $C_{12}H_{12}ClFN_4O_3$]: C 45.80, H 3.84, N 17.80 [%].

EXAMPLE 16

5-Fluoro-3,4-dihydro-2,4-dioxo-N-[5-(1-pyridinio)pentyl]-1(2H)-pyrimidinecarboxamide bromide:

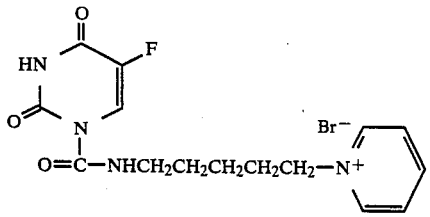

5-Bromopentyl isocyanate (3.00 g, 15.6 mmol) and 5-fluorouracil (2.04 g, 15.7 mmol) were added into pyridine (25 ml), and the mixture was stirred and refluxed at 80° C. to 100° C. for 3 hours.

After cooling the reactant, the residue obtained under reduced pressure was washed with chloroform, and vacuum-dried. 5-Fluoro-3,4-dihydro-2,4-dioxo-N-(5-(1-pyridinio)pentyl]-1(2H)-pyrimidinecarboxamide bromide (3.68 g, 9.17 mmol) was obtained.

Yield: 59%, Melting point: 132°~135° C.

IR$_{max}$ (KBr disk): 3430, 3300(NH), 3060(=CH—), 2950, 2860(C—H), 1755, 1720, 1675(>=O), 1245 (=CF—) [cm$^{-1}$].

Element analysis: Found C 44.73, H 4.57, N 13.25 [%]; Calculated [for $C_{15}H_{18}BrFN_4O_3$]: C 44.90, H 4.52, N 13.96 [%].

EXAMPLE 17

5-Fluoro-3,4-dihydro-2,4-dioxo-N-[3-(1-pyridinio)propyl]-1(2H)-pyrimidinecarboxamide chloride:

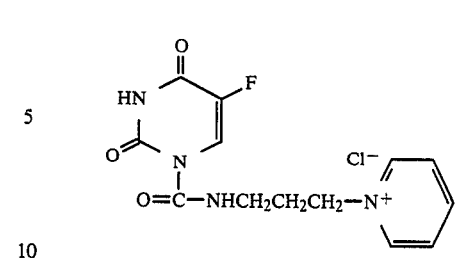

3-Chloropropyl isocyanate (2.71 g, 22.7 mmol) and 5-fluorouracil (2.95 g, 22.7 mmol) were added into pyridine (20 ml), and stirred and refluxed at 90° C. for 3 hours.

After cooling the reactant, benzene was added. The obtained crystals were filtered, and washed with benzene, and then with chloroform, 5-Fluoro-3,4-dihydro-2,4-dioxo-N-[3-(1-pyridinio)propyl]-1(2H)-pyrimidinecarboxamide chloride (2.82 g, 8.58 mmol) was obtained.

Yield: 38%, Melting point: 80°~105° C.

IR$_{max}$ (KBr disk): 3440(NH), 3130, 3070 (=CH—), 1710~1750, 1640~1710(>=O), 1245(=CF—) [cm$^{-1}$].

Element analysis: Found C 47.38, H 4.66, N 16.44 [%]; Calculated [for $C_{13}H_{14}ClFN_4O_3$]: C, 47.50, H 4.29, N 17.04 [%].

EXAMPLE 18

5-Fluoro-3,4-dihydro-2,4-dioxo-N-{6-[3-(3-pyridyl)ureido]hexyl}-1(2H)-pyrimidinecarboxamide:

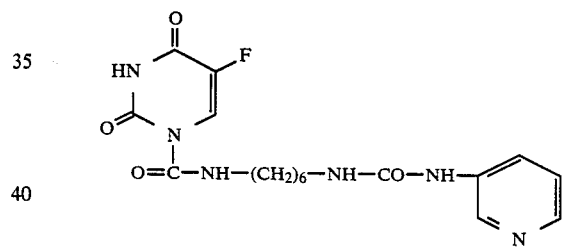

1,6-Hexamethylene diisocyanate (1.29 g, 7.67 mmol) was added into pyridine (20 ml). 5-Fluorouracil (1.00 g, 7.69 mmol) was added into the solution little by little for 20 minutes. Then the mixture was stirred and reacted at 90° C. for one hour.

After cooling the reactant, the residue obtained under reduced pressure was dissolved into chloroform, and insoluble parts were removed. Thus obtained solution of the derivative having an isocyanate group was concentrated to about 10 ml. 3-Aminopyridine (0.72 g, 7.65 mmol) was added into the solution. After dissolving, the mixture was refluxed for one minute.

After cooling the reactant, obtained crystals were filtered, washed with chloroform, then washed with hot acetonitrile and vacuum-dried. 5-Fluoro-3,4-dihydro-2,4-dioxo-N-{6-[3-(3-pyridyl)ureido]hexyl}-1(2H)-pyrimidinecarboxamide (1.41 g, 3.59 mmol) was obtained.

Yield: 47%, Melting point: 180°~183° C.

R$_{max}$ (KBr disk): 3400, 3330(NH), 3100 (=CH—), 2940, 2850(C—H), 1740, 1695, 1665(>=O), 1230(=CF—) [cm$^{-1}$].

Element analysis: Found C 52.97, H 5.55, N 21.48 [%]; Calculated [for $C_{17}H_{21}FN_6O_4$]: C 52.04, H 5.39, N 21.42 [%].

EXAMPLE 19

5-Fluoro-3,4-dihydro-2,4-dioxo-N-{6-[3-(2-pyridyl)ureido]hexyl}-1(2H)-pyrimidinecarboxamide:

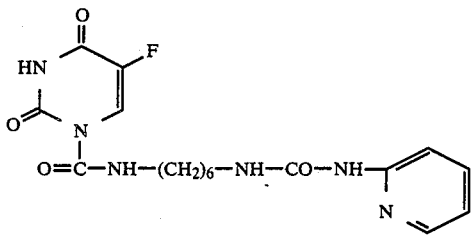

1,6-Hexamethylene diisocyanate (2.59 g, 15.4 mmol) was added into pyridine (30 ml). 5-Fluorouracil (2.00 g, 15.4 mmol) was added into the solution little by lttle for 30 minutes. Then, the mixture was stirred and reacted at 90° C. for one hour.

After cooling the reactant, the residue obtained under reduced pressure was dissolved into chloroform, then insoluble parts were removed and concentrated to about 15 ml. 2-Aminopyridine (1.45 g, 15.4 mmol) was added into thus obtained solution of the derivative having an isocyanate group and stirred at room temperature for 10 minutes. The obtained crystals were removed. After concentrating the filtrate, obtained crystals were washed with chloroform and vacuum-dried, 5-Fluoro-3,4-dihydro-2,4-dioxo-N-{6-[3-(2-pyridyl)ureido]hexyl}-1(2H)-pyrimidinecarboxamide (1.81 g, 4.61 mmol) was obtained.

Yield: 30%, Melting point: 177°~181° C.

IR$_{max}$ (KBr disk): 3450, 3410, 3300(NH), 3050(=CH—), 2940, 2850(C—H), 1740, 1690, 1675(>=0), 1230(=CF—) [cm$^{-1}$]

Element analysis: Found C 52.33, H 5.49, N 20.72 [%]; Calculated [for $C_{17}H_{21}FN_6O_4$]: C 52.04, H 5.39, N 21.42 [%].

EXAMPLE 20

5-Fluoro-3,4-dihydro-2,4-dioxo-N-{6-[3-(4-sulfamoylphenyl)ureido]hexyl}-1(2H)-pyrimidinecarboxamide:

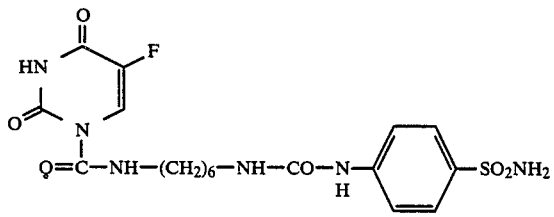

1,6-Hexamethylene diisocyanate (2.59 g, 15.4 mmol) was added into benzene (25 ml) and the solution was refluxed. 5-Fluorouracil (2.00 g, 15.4 mmol) dissolved in pylidine (20 ml) was added into the solution little by little for 20 minutes. Then, the mixture was stirred and reacted for one hour.

After cooling the reactant, the residue obtained under reduced pressure was dissolved into chloroform, and then insoluble parts were removed. The filtrate was concentrated, and the residue was washed with hexane. Tetrahydrofuran (20 ml) was added into the obtained crude material of derivative containing isocyanate group to dissolve, and sulfanilamide (2.63 g, 15.3 mmol) was added to the solution. The mixture was refluxed for one hour. After cooling, the reactant was concentrated under reduced pressure, and chloroform was added. The obtained crystals were filtered, washed with chloroform and then acetone. Hot methanol was added into the crystals to dissolve the crystals and to remove insoluble materials. The filtrate was washed and vacuum-dried. 5-Fluoro-3,4-dihydro-2,4-dioxo-N-{6-[3-(4-sulfamoylphenyl)ureido]hexyl}-1(2H)-pyrimidine-carboxamide (1.08 g, 2.30 mmol) was obtained.

Yield: 15%, Melting point: 181°~184° C.

IR$_{max}$ (KBr disk): 3400, 3350, 3260(NH), 3130(=C), 2960, 2890(C—H), 1750, 1710, 1685(>=0), 1340, 1160(SO$_2$), 1240(=CF—) [cm$^{-1}$].

Element analysis: Found C 46.37, H 5.24, N 17.32 [%]; Calculated [for $C_{18}H_{23}FN_6O_6S$]: C 45.95, H 4.93, N 17.86 [%].

EXAMPLE 21

5-Fluoro-3,4-dihydro-2,4-dioxo-N-{6-[3-(3-dimethylaminopropyl)ureido]hexyl}-1(2H)-pyrimidinecarboxamide:

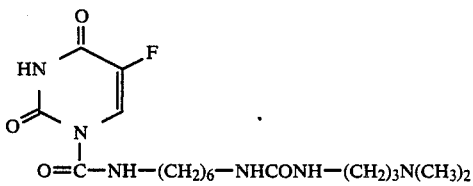

1,6-Hexamethylene diisocyanate (2.59 g, 15.4 mmol) was added into pyridine (25 ml). 5-Fluorouracil (2.00 g, 15.4 mmol) was added into the solution little by little for 20 minutes at 90° C. Then, the mixture was stirred and reacted for one hour.

After cooling the reactant, the residue obtained under reduced pressure was dissolved into chloroform, and insoluble parts were removed. The filtrate was concentrated to about 10 ml. N,N-Dimethyl-1,3-propanediamine (1.57 g, 15.4 mmol) was added into the obtained solution of derivative having isocyanate group, and the mixture was stirred and reacted for 10 hours at room temperature. After concentrating the solution under reduced pressure, chloroform was added into the obtained residue. The separated viscous material was washed with chloroform and vacuum-dried. 5-Fluoro-3,4-dihydro-2,4-dioxo-N-{6-[3-(3-dimethylaminopropyl)ureido]hexyl}-1(2H)-pyrimidinecarboxamide (4.20 g, 10.5 mmol) was obtained.

Yield: 68%, Melting point: 70°~81° C.

IR$_{max}$ (KBr disk): 3420(NH), 3120(=CH—), 2960, 2880(C—H), 1740, 1690(>=0), 1250(=CF—) [cm$^{-1}$].

Element analysis: Found C 50.41, H 7.06, N 19.36 [%]; Calculated [for $C_1H_{29}FN_6O_4$]: C 50.99, H 7.30, N 20.99 [%].

EXAMPLE 22

5-Fluoro-3,4-dihydro-2,4-dioxo-N-{6-[3-nicotinamidoureido]hexyl}-1(2H)-pyrimidinecarboxamide:

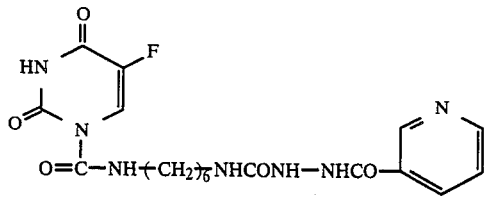

1,6-Hexamethylene diisocyanate (2.59 g, 15.4 mmol) was added into pyridine (25 ml). 5-Fluorouracil (2.00 g, 15.4 mmol) was added into the solution little by little for 20 minutes at 90° C. Then, the mixture was stirred and reacted for one hour.

After cooling the reactant, the residue obtained under reduced pressure was dissolved into chloroform, and insolubles were removed. The filtrate was concentrated to about 10 ml. Nicotinoylhydrazide (2.10 g, 15.3 mmol) was added into the obtained filtrate and the mixture was refluxed for 20 minutes. After cooling, crystals were filtered. The obtained crystals were washed with chloroform, and vacuum-dried. 5-Fluoro-3,4-dihydro-2,4-dioxo-N-{6-[3-nicotinamidoureido]hexyl}-1(2H)-pyrimidinecarboxamide (2.05 g, 4.71 mmol) was obtained.

Yield: 31%, Melting point: 138°~147° C.

IR$_{max}$ (KBr disk): 3200~3400(NH), 3100 (=CH—), 2940, 2860(C—H), 1740, 1700, 1660(>=O), 1250(=CF—) [cm$^{-1}$].

Element analysis: Found C 50.33, H 5.39, N 22.88 [%]; Calculated [for C$_{18}$H$_{22}$FN$_7$O$_5$]: C 50.82, H 5.21, N 23.05 [%].

EXAMPLE 23

5-Fluoro-3,4-dihydro-2,4-dioxo-N-{6-[3-isonicotinamidoureido]hexyl}-1(2H)-pyrimidinecarboxamide

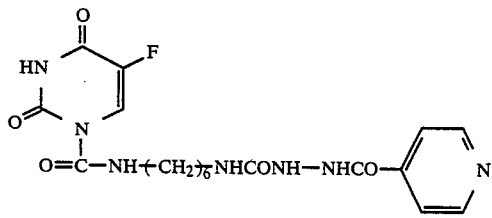

1,6-Hexamethylene diisocyanate (2.59 g, 15.4 mmol) was added into pyridine (25 ml). 5-Fluorouracil (2.00 g, 15.4 mmol) was added into the solution little by little for 20 minutes at 90° C. Then, the mixture was stirred and reacted at 90° C. for one hour.

After cooling the reactant, the residue obtained under reduced pressure was dissolved into chloroform, and insolubles were removed. The filtrate was concentrated to about 10 ml. Isonicotinoylhydrazide (2.10 g, 15.3 mmol) was added into the obtained filtrate and the mixture was refluxed for 30 minutes. After cooling, crystals were filtered. The obtained crystals were washed with hot methanol, and hot pyridine was added to dissolve the crystals. The resulting insolubles were removed and the filtrate was concentrated under reduced pressure. The obtained crystals were washed with methanol and vacuum-dried. 5-Fluoro-3,4-dihydro-2,4dioxo-N-{6-[3-isonicotinamidoureido]hexyl}-1(2H)-pyrimidinecarboxamide (1.56 g, 3.58 mmol) was obtained.

Yield: 23%, Melting point: 185°~197° C.

IR$_{max}$ (KBr disk): 3400, 3300(NH), 3100(=CH—), 2940, 2860(C—H), 1745, 1700, 1670(>=O), 1250(=CF—) [cm$^{-1}$].

Element analysis: Found C 50.72, H 5.17, N 23.24 [%]; Calculated [for C$_{18}$H$_{22}$FN$_7$O$_5$]: C 50.82 H 5.21, N 23.05 [%].

EXAMPLE 24

5-Fluoro-3,4-dihydro-2,4-dioxo-N-{6-[3-(quinoline-3-yl)ureido]hexyl}-1(2H)-pyrimidinecarboxamide

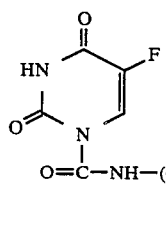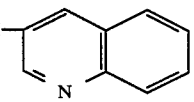

1,6-Hexamethylene diisocyanate (3.87 g, 23.0 mmol) was added into pyridine (60 ml). 5-Fluorouracil (2.98 g, 22.9 mmol) was added into the solution little by little for 30 minutes. Then, the mixture was stirred and reacted at 90° C. for one hour.

After cooling the reactant, the residue obtained under reduced pressure was dissolved into chloroform, and insolubles were removed. The filtrate was concentrated to about 30 ml. 3-Aminoquinoline (3.32 g, 23.0 mmol) was added into the obtained filtrate and the mixture was refluxed for 30 minutes. The obtained crystals were filtered and washed with hot acetonitrile and vacuum-dried. 5-Fluoro-3,4-dihydro-2,4-dioxo-N-{6-[3-(quinoline-3-yl)ureido]hexyl}-1(2H)-pyrimidinecarboxamide (6.20 g, 14.0 mmol) was obtained.

Yield: 61%, Melting point: 190°~195° C.

IR$_{max}$ (KBr disk): 3400, 3300(NH), 3040(=C—), 1740, 1705, 1680(>=O), 1260(=CF—) [cm$^{-1}$].

Element analysis: Found C 57.30, H 5.52, N 18.40 [%];

EXAMPLE 25

5-Fluoro-3,4-dihydro-2,4-dioxo-N-{6-[3-(benzothiazole-2-yl)ureido]hexyl}-1(2H)-pyrimidinecarboxamide

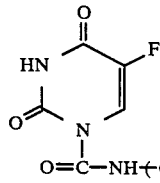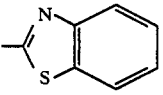

1,6-Hexamethylene diisocyanate (3.76 g, 22.4 mmol) was added into pyridine (60 ml). 5-Fluorouracil (2.98 g, 22.9 mmol) was added into the solution little by little for 30 minutes at 90° C. Then, the mixture was stirred and reacted at 90° C. for one hour.

After cooling the reactant, the residue obtained under reduced pressure was dissolved into chloroform, and insolubles were removed. The filtrate was concentrated to about 30 ml. 2-Aminobenzothiazole (3.35 g, 22.3 mmol) was added into the obtained filtrate which contained an isocyanate derivative, and the mixture was refluxed for one hour. After cooling, crystals were filtered. The obtained crystals were washed with methanol and vacuum-dried. 5-Fluoro-3,4-dihydro-2,4-dioxo-N-{6-[3-(benzothiazole-2-yl)ureido]hexyl}-1(2H)-pyrimidinecarboxamide (4.04 g, 9.02 mmol) was obtained.

Yield: 40%, Melting point: 256°~262° C.

$IR_{max}$ (KBr disk): 3380, 3275(NH), 3180, 3050(=CH—), 1750, 1720, 1690(>=0), 1260(=CF—) [cm$^{-1}$].

Element analysis: Found C 50.68, H 4.96, N 19.00 [%]; Calculated [for $C_{19}H_{21}FN_6O_4S$]: C 50.89, H 4.72, N 18.74 [%].

EXAMPLE 26

5-Fluoro-3,4-dihydro-2,4-dioxo-N-pyridiniomethyl-1(2H)-pyrimidinecarboxamide chloride:

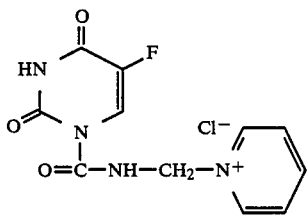

Chloromethyl isocyanate (10.6 g, 116 mmol) and 5-fluorouracil (7.56 g, 58.2 mmol) were added into pyridine (100 ml). Then, the mixture was stirred and reacted under reflux for 15 minutes. After cooling the reactant, the obtained crystals were washed with pyridine, and then toluene, and vacuum-dried. 5-Fluoro-3,4-dihydro-2,4-dioxo-N-pyridiniomethyl-1(2H)-pyrimidinecarboxamide chloride (17.0 g, 56.5 mmol) was obtained.

Yield: 97%, Melting point: 171°~177° C.

$IR_{max}$ (KBr disk9: 3300(NH), 3100, 3055(=CH—), 1765, 1730, 1685(>=0), 1255(=CF—) [cm$^{-1}$].

Element analysis: Found C 43.72, H 3.62, N 18.90 [%]; Calculated [for $C_{11}H_{10}FClN_4O_3$]: C 43.94, H 3.35, N 18.63 [%].

[Antitumor Effect Test]

Leukosis cells of P-388 mouse of $1 \times 10^6$/mouse were grafted into the abdomen of $CDF_1$ or $BDF_1$ mouse, and the fixed quantity of the compound of this invention was successively dosed into the abdomen for 5 days.

Each 6 mice per dose level as test groups and 30~33 mice as control groups were used. Effect of antitumor was decided by the ratio of survival days (T/C), the result is shown in Table 1.

The ratio of survival days T/C =

$$\frac{\text{Average survival day of dosed groups}}{\text{Average survival day of control groups}} \times 100(\%)$$

TABLE 1

| Dosed compound (1) | Dose mg/kg | T/C % | | Dosed compound (1) | Dose mg/kg | T/C % | |
|---|---|---|---|---|---|---|---|
| Experiment 1 | 240 | 152 | 129 | Experiment 17 | 120 | 161 | 120 |
| | 120 | 152 | 124 | | 60 | 138 | 131 |
| | 60 | 138 | 137 | | 30 | 130 | 115 |
| | 30 | 129 | 129 | | 15 | | |
| Experiment 2 | 120 | 128 | 92 | Experiment 18 | 15 | 139 | |
| | 60 | 166 | 175 | | 7.5 | 138 | |
| | 30 | | 149 | | 3.75 | 131 | |
| | 15 | | 127 | | 1.87 | 124 | |
| | | | | | 0.94 | 115 | |
| | | | | | 0.47 | 110 | |
| Experiment 3 | 400 | | 153 | Experiment 19 | 240 | 198 | 109 |
| | 240 | 170 | 142 | | 120 | 164 | 160 |
| | 120 | 136 | 128 | | 60 | 154 | 151 |
| | 60 | 135 | 117 | | 30 | | |
| | 30 | 123 | 116 | | | | |
| Experiment 4 | 400 | | 128 | Experiment 20 | 240 | 112 | 102 |
| | 240 | 148 | 111 | | 120 | 111 | 96 |
| | 120 | 118 | 111 | | 60 | 110 | |
| | 60 | 115 | | | 30 | 95 | |
| | 30 | 117 | | | | | |
| Experiment 13 | 120 | 147 | 132 | Experiment 21 | 60 | | 120 |
| | 60 | 132 | 115 | | 30 | 142 | 123 |
| | 30 | 117 | 103 | | 15 | | 120 |
| Experiment 14 | 120 | | | Experiment 22 | 400 | | 127 |
| | 60 | 215 | 212 | | 240 | 140 | 99 |
| | 30 | | 171 | | 120 | 128 | 115 |
| | 15 | | 169 | | 60 | 113 | 126 |
| | | | | | 30 | 113 | |
| | | | | | 15 | | |
| Experiment 16 | 30 | 120 | | Experiment 23 | 240 | 138 | 123 |
| | 15 | 120 | | | 120 | 124 | 115 |
| | 7.5 | 112 | | | 60 | 119 | |
| | | | | | 30 | 109 | |

[Acute Toxity Test]

$LD_{50}$ measured by dosing the compounds which was obtined by each experiment are shown in Table 2.

TABLE 2

| Dosed Compound | $LD_{50}$ (mg/kg) | Dosed Compound | $LD_{50}$ (mg/kg) |
|---|---|---|---|
| Experiment 1 | >240 | Experiment 17 | 240 |
| 2 | 240 | 18 | >30 |
| 3 | >400 | 19 | >240 |
| 4 | >400 | 20 | >240 |
| 13 | 240 | 21 | |
| 14 | 120 | 22 | >400 |
| 16 | 60 | 23 | >240 |

What is claimed is:

1. A compound of the formula

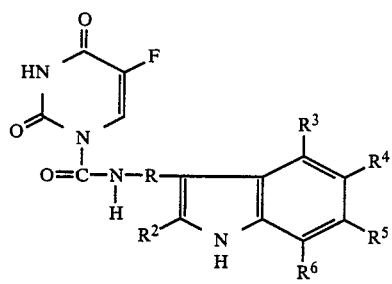

wherein R is a covalent bond, —CH$_2$, —(CH$_2$)$_2$— or —CH(COOC$_2$H$_5$)CH$_2$—; each of R$^2$, R$^3$, R$^4$, R$^5$ and R$^6$ is a hydrogen atom, a halogen atom, a methyl group or a methoxy group.

2. A compound as claimed in claim 1 wherein all of R$^2$, R$^3$, R$^4$, R$^5$ and R$^6$ are hydrogen atoms.

3. A compound as claimed in claim 1 wherein R$^2$, R$^3$, R$^5$ and R$^6$ are hydrogen atoms and R$^4$ is a halogen atom or a methoxy group.

4. A compound as claimed in claim 1 wherein R$^2$ and R$^6$ are hydrogen atoms and R$^3$, R$^4$ and R$^5$ are methoxy groups.

5. A compound as claimed in claim 1 wherein R$^2$ is a methyl group and R$^3$, R$^4$, R$^5$ and R$^6$ are hydrogen atoms.

* * * * *